United States Patent [19]

Gausa

[11] Patent Number: 4,879,000
[45] Date of Patent: Nov. 7, 1989

[54] PROCESS FOR DETERMINING DIMENSION ERRORS

[75] Inventor: Alexander Gausa, Bielefeld, Fed. Rep. of Germany

[73] Assignee: Feldmuehle Aktiengesellschaft, Duesseldorf, Fed. Rep. of Germany

[21] Appl. No.: 178,140

[22] Filed: Apr. 6, 1988

[30] Foreign Application Priority Data

Apr. 18, 1987 [DE] Fed. Rep. of Germany ....... 3713279

[51] Int. Cl.$^4$ .............................................. D21F 11/00
[52] U.S. Cl. .................................... 162/198; 162/110; 162/140; 250/571; 250/572; 356/429; 356/430; 356/431
[58] Field of Search ............... 162/198, 109, 110, 140; 250/571, 572; 356/429, 430, 431

[56] References Cited

U.S. PATENT DOCUMENTS

| | | | |
|---|---|---|---|
| 3,843,890 | 10/1974 | Anthony | 250/572 |
| 3,919,560 | 11/1975 | Nopper | 250/571 |
| 4,265,545 | 5/1981 | Slaker | 250/572 |
| 4,557,786 | 12/1985 | Stock et al. | 250/571 |
| 4,570,074 | 2/1986 | Jette | 250/572 |

FOREIGN PATENT DOCUMENTS 284468 1/1971 U.S.S.R. ........................... 356/430

Primary Examiner—Peter Chin
Attorney, Agent, or Firm—Felfe & Lynch

[57] ABSTRACT

A method of testing security papers with respect to the positions of a safety thread and water marks to detect errors in the paper is performed by a linewise scanning of a finished paper web. The web has at least two point like measuring marks inserted into it in addition to the water marks, whereby impulses which are originated from these measuring marks are evaluated and the sheet width and the sheet distortion are calculated by comparing the x-y positions of the individual measuring marks with each other. The measuring marks are sharpe edged and rich in contrast. The given edge impulse is evaluated.

9 Claims, 4 Drawing Sheets

Fig. 1

PROCESS FOR DETERMINING DIMENSION ERRORS

FIELD OF THE INVENTION

The invention relates to a method for picking up dimension errors and distortion of papers provided with water marks. In particular, security papers, such as bank notes, may be tested according to the inventive method.

BACKGROUND OF THE INVENTION

Bank notes are generally made with a paper which is provided with water marks and safety threads. The safety threads and water mark or marks in the finished bank note should be disposed in a defined area. During the making of the crude paper in the paper machine, a certain distortion of the paper may occur. Also later during cutting of the paper on the ruler cutter, as well as on the transverse cutter, elongations may, for example, be inserted into the paper because of inaccurate feeding or an irregular moisture profile. Thus, the water marks are no longer in the same predetermined position.

In order to have a control possibility it is known to insert a so-called tracking-line, that is, a dashed-dotted marking in the form of a water mark at the edge of the paper web and, if need be, in the center of the paper web during the manufacturing process. Furthermore, control marks may be disposed transversely to the paper web for the transverse cutter.

In order to find dimension changes or distortion errors, in the sheets, it is customary at present to manually place the individual sheets after the transverse cutting, with one cutting edge or a longitudinal edge on a transparent plate which is lit from below and visually examine whether the position of the water marks and the position of the safety thread coincides with the predetermined position. As customary each individual sheet is provided with a plurality of copies, whereby the control marks and the tracking-line are outside of these copies. Hitherto, the paper edge or the tracking-line is used as a reference edge when cutting the web in the longitudinal roller and the control mark is used when cutting the web in the transverse cutter. However, neither marking is suitable for an accurate dimensioning.

SUMMARY OF THE INVENTION

It is therefore an object of the invention to improve the prior art inspection of security papers by automating the examination of the paper during the processing, as well as on the paper machine, to increase the examining speed considerably, to improve examining accuracy and thereby to enable the maintaining of lower tolerances.

This object of the inventive method is achieved by inserting at least two point like measuring marks per sheet area as water marks, being disposed opposite each other in the sheet intermediate area in addition to the provided water marks during the paper making in the wet portion of the paper machine. The finished paper web or the sheet papers are scanned, the reflected or permeated light is picked up by a photoelectric converter and the pulses originating from the measuring marks are evaluated in an analog signal by a measuring mark computer. Values established by the measuring mark computer are transmitted to an evaluation computer which compares the x-y positions of the individual measuring marks with respect to each other and thereby calculates the length, the width and any distortion of the sheet.

The term "sheet area" within the meaning of the subject invention means the area of a web of paper which forms the sheet after being cut into a sheet paper. In general it is the area which is disposed between two transverse cutter marks.

The distance between the two point like measuring marks, which are disposed in a defined distance with respect to each other, is measured and this distance is compared to a predetermined fixed value for the width of the sheet to get an answer whether a distortion of the sheet has occurred because of a transverse elongation. The same is true for successive measuring marks with respect to a change in the sheet length.

In contrast to using only one measuring mark to scan in one line, i.e., during a scan, the simultaneous use of a plurality of sheet areas to be scanned which are distributed over the width of the material web establishes that the sheet or the sheet area is distorted. This distortion may be different across the width of the web of material, therefore, for each sheet area or sheet one evaluation and one proposition are required. The number of scans, wherein only one measuring mark is picked up in the sheet area or also the number of the scans which are performed until picking up a measuring mark which is mounted in a different position, actually the second measuring mark, are a measurement for the size of the distortion, i.e. it can be exactly calculated therefrom.

It is important for the evaluation that the measuring marks are sharp edged and rich in contrast, so that a sharp pulse is delivered. Therefore, the measuring marks are advantageously inserted in form or recesses with a square base face which have a side length between 2 and 5 mm. The upper limit of these squares is thereby less critical than the fact that the squares must be sharp edged and rich in contrast, since the evaluation is based on the so-called edge pulse.

The sharp edge is required to trigger an edge pulse which is always positioned on exactly the same place. Only by the presence of these sharp locally limited markings, is an exact measuring and evaluation possible. The further important point is the contrast. Without a sufficient contrast which sufficiently rises above the general noise level, an exact evaluation is not possible. Therefore, the invention provides that the depth of the measuring marks is 40 to 80% of the paper thickness. This data is of particular importance when examining in transmission, but also achieves usable values in the remission testing.

A preferred embodiment of the invention provides that the scanning is performed by a flying light point which, in accordance with an advantageous embodiment of the invention, has a diameter between 500 and 1,200 microns ($\mu$m). The closer one operates on the lower light point diameter, the larger is the exactness which can be achieved during the evaluation.

When fixing the diameter of the flying light point the cloudiness of the paper is also considered, i.e., the fiber distribution in the paper, also goes into the evaluation. If one operates with a very small light point and if an extremely cloudy paper is involved, the cloudiness results in a high interference or noise level, since only a small area is picked up, so that a strong difference in the reflected or transmitted light results in a corresponding deflection or pulse. Therefore, when working with severely cloudy paper it is recommended to operate with a light point dimension which is more in the upper range, for example, at 1,000 microns.

A preferred embodiment of the invention provides that the scanning of individual areas is performed with a different density. This embodiment is preferred because when examining security papers, safety threads are present in addition to the water marks. Thereby, the water marks as well as the safety threads deliver pulses whose amplitudes are clearly above the vellum range, which during the evaluation is then interpreted as an error. The term "vellum range" is understood to mean in security papers the range in which the crude paper has no markings, inerts etc.

Naturally, this range must be also examined, since it also may contain errors during the paper making. Because of the invention the areas in which the water marks, measuring marks or safety threads are present can be scanned with a lower sensitivity. The pulses which originate from safety threads, water marks and measuring marks can be kept so low that they are below the threshold which could result in an error. Therefore, when evaluating errors these pulses are suppressed. Alternatively, it is naturally also possible to scan the areas wherein no measuring marks are present or are not expected with a higher sensitivity. In order not to be fixed for defined areas, an advantageous embodiment of the invention provides that the areas of the face to be scanned and which should be scanned with higher or lower sensitivity are selectable. Therefore, the measuring marks in accordance with a preferred embodiment of the invention are disposed in areas outside of the safety threads and the provided water marks, i.e., in the intermediate area of the sheet.

BRIEF DESCRIPTION OF THE DRAWINGS

The invention will be explained in detail in conjunction with the appended drawings.

DETAILED DESCRIPTION OF THE PREFERRED EMBODIMENTS

Figure 1:
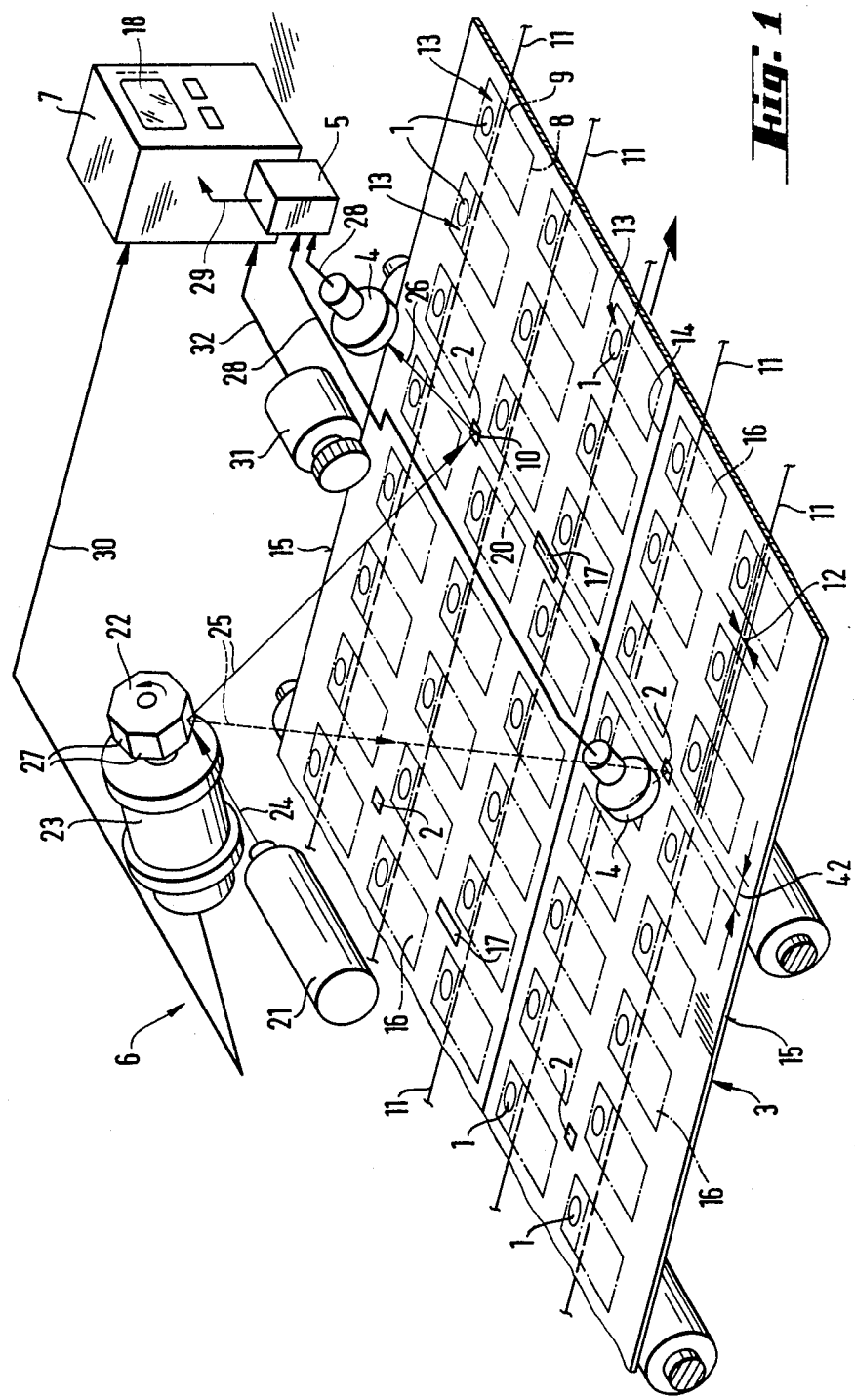
FIG. 1 is a schematic perspective view of a test device used according to the invention and having a reflection measuring means.

The paper web 3, which is made on the paper machine (not shown), is provided with water marks 1 and measuring marks 2 which are also inserted in the form of water marks. This paper web 3 is wound up in the paper machine on so-called tambours which, after a longitudinal and width separation, are rewound onto mother rolls on a roll cutter and delivered to the security paper manufacturing in such a manner. Depending on the type of the security paper to be made they are already cut into copies by means of a transverse cutter, i.e., cut into sheet paper which are then printed or are previously printed in the rotary printing process and are then cut into copies 16 by means of a transverse cutter.

The endless web, i.e., the paper web 3 as well as the copy 16 contains a plurality of water mark areas 13 of which at least one can be found later in the finished bank note, also at least one safety thread area 12 is provided which later can also be found in the finished bank note.

The insertion of the safety thread 11 as well as the insertion of the water mark 1 is performed in the wet portion of the machine, that is, at a point in time when the forming of the paper web 3 is not yet finished, and when a displacement of the safety thread 11 and an impairment of the clarity of the water marks 1 may occur due to fiber movements. For this reason tolerance fields must be determined, within which the water mark 1 must be present, on the one hand, and also the safety thread 11 in paper web 3, on the other hand. These tolerance fields are designated as a safety thread area 12 or a water mark area 13.

Since the paper edges 15 as generated on the paper machine are always somewhat flowing they may be used only for coarse controls in form of a base line. It is therefore customary in security paper making to provide a reference line in the paper web 3 which is also inserted through the screen of the paper machine which forms the paper web 3 or a dropper which runs thereabove. This reference line is designated as a tracking-line 14. It may be disposed in proximity to the longitudinal edge, i..e., in proximity to paper edge 15, but it is also possible to move it further inside the paper web, so that it runs between two copies 16.

In addition to the inserting of the tracking line 14 the state of the art also provides insertion of control marks 17. Hitherto, the tracking line 14 had been used for controlling the roll cutters, i.e., the units which performed a longitudinal separation of the tambour or the mother rolls, while the control mark 17 is used for controlling the transverse cutter which performs one cut at each control mark 17. If the paper is elongated, sheets 33 are generated which are a sheet length 8 which is beyond the required length and can therefore not be used. If the paper is shrunk, a correspondingly short sheet 33 is generated which is too short. However, these controls do not suffice for an accurate dimensioning of a copy 16 to the sheet length 8 and sheet width 9, so that the individual copies 16 had to be tested hitherto manually with respect to length, presence of water marks 1 and safety thread 11, as well as with respect to the disposition of the water marks 1 in the water mark area 13 and the presence of the safety thread 11 in the safety thread area 12 whereby also eventual errors in the paper were also examined, since an automatic or mechanical paper testing on account of the inserted water marks 1 and the safety threads 11 were not possible.

By inserting sharp edged measuring marks 2 into the paper web 3 the basis for electronic, automatic testing is provided.

From a laser 21, which is mounted in a measuring head 6, a laser beam 24 is directed to the mirror wheel 22 which is driven by the mirror wheel motor 23. The scanning beam 25 which is reflected by the bevels 27 of the rotating mirror wheel 22 forms a scanning line 2 on the paper web 3 due to the movement of the flying light point 10 extending over the total width of the paper web 3.

The light which is reflected from the paper web 3 is fed as a reflection beam 26 or a transmission beam 26', if the operation is performed in a transillumination process, to the photoelectric converter 4 or 4' and is fed from there through the measuring line 28,28' to the measuring mark computer 5 which is connected through the connecting line 29 with the evaluation computer 7 with an integrated monitor 18.

The evaluation computer 7 is also connected through a pulse line 30 with the measuring head 6 having an associated timing rod (not shown). This timing rod delivers pulses with the width of the paper web is sectioned into uniform small fields taking into consideration the given angle of the scanning beam 25, so that the given position of the flying light point 10 can be defined on the paper web 10.

Figure 2:
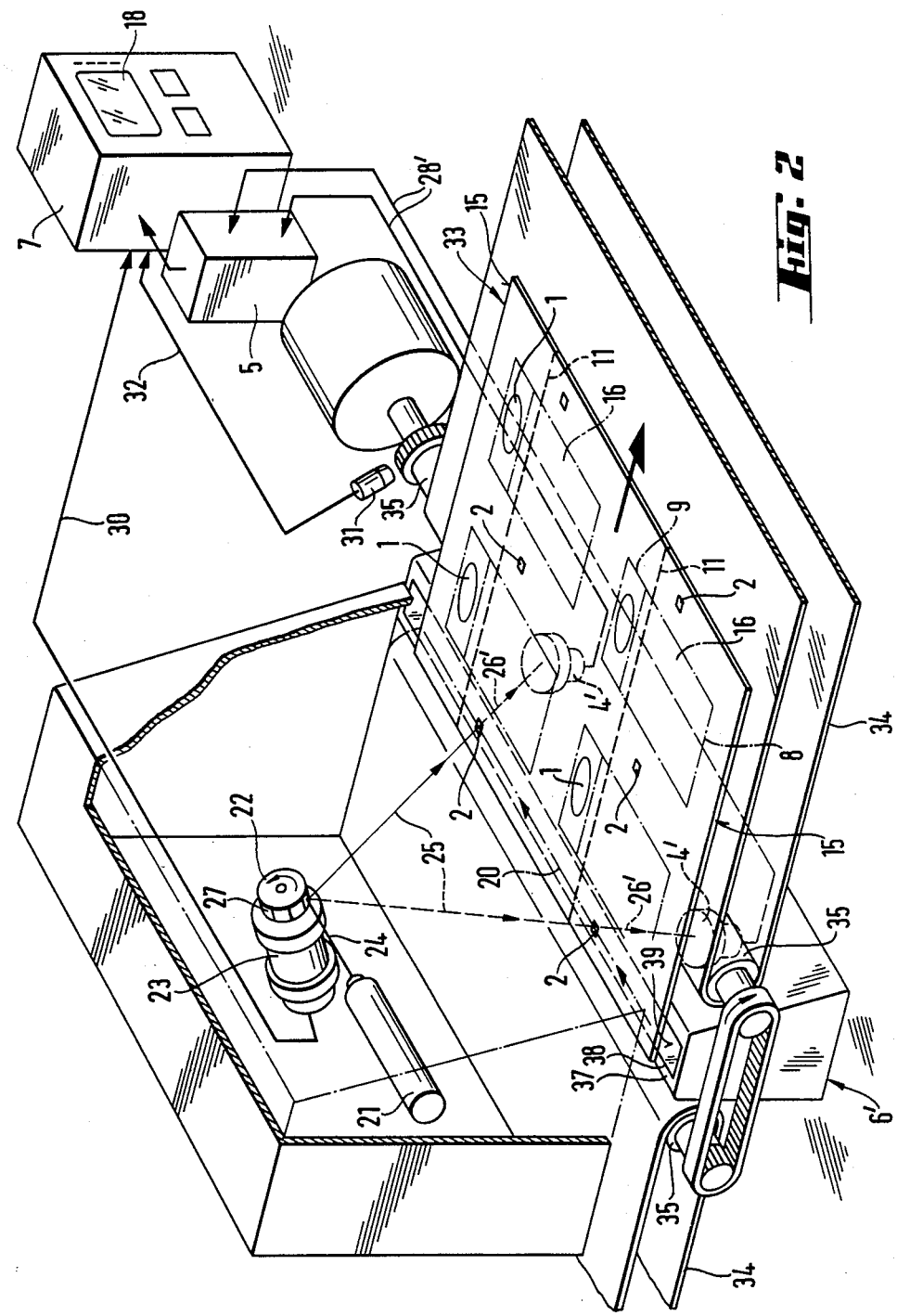
FIG. 2 is a schematic perspective view of the test device of FIG. 1 having a transmission measuring means.

If, as illustrated in FIG. 2, individual sheets 33 are tested which contain a plurality of copies 16 the same are disposed on conveyor belts 34 which are guided by rollers 35 and are driven by an electromotor 36 and feed the sheets 33 over the cover 37 of the measuring head 6' which is mounted between the conveyor belts 34 below paper web 33, whereby this measuring head 6' is provided with a slot 38 extending over the full paper web width and is covered with a glass plate 39. The scanning beam 25 passes through slot 38 and the glass plate 39 is picked up by the photoelectric converter 4' and fed through the measuring line 28' to the measuring mark computer 5 which in turn is connected with the evaluation computer 7. The position of sheets 33 may be determined by comparing the x-y coordinates of the measuring marks 2 with pulses which are fed through the impulse line 22 from the impulse generator 31 to the evaluation computer 7.

The result can be made visible by means of the monitor 18 which is integrated into the evaluation computer 7, i.e., that deviations with respect to sheet length 8, sheet width 9, the position of the water marks 1 or the safety thread 11 as well as a possible distortion is made graphically visible or in the form of tables. By comparison with the predetermined constants which are selectable and by selectable tolerance fields with respect to these constants, the difference between good and non-usable copies 16 can be determined. Resulting signals therefrom may be used for marking the sheet 33 which should be sorted out or may be used directly for removing the individual sheets 33 by means of an impulse shunt.

Figure 3:
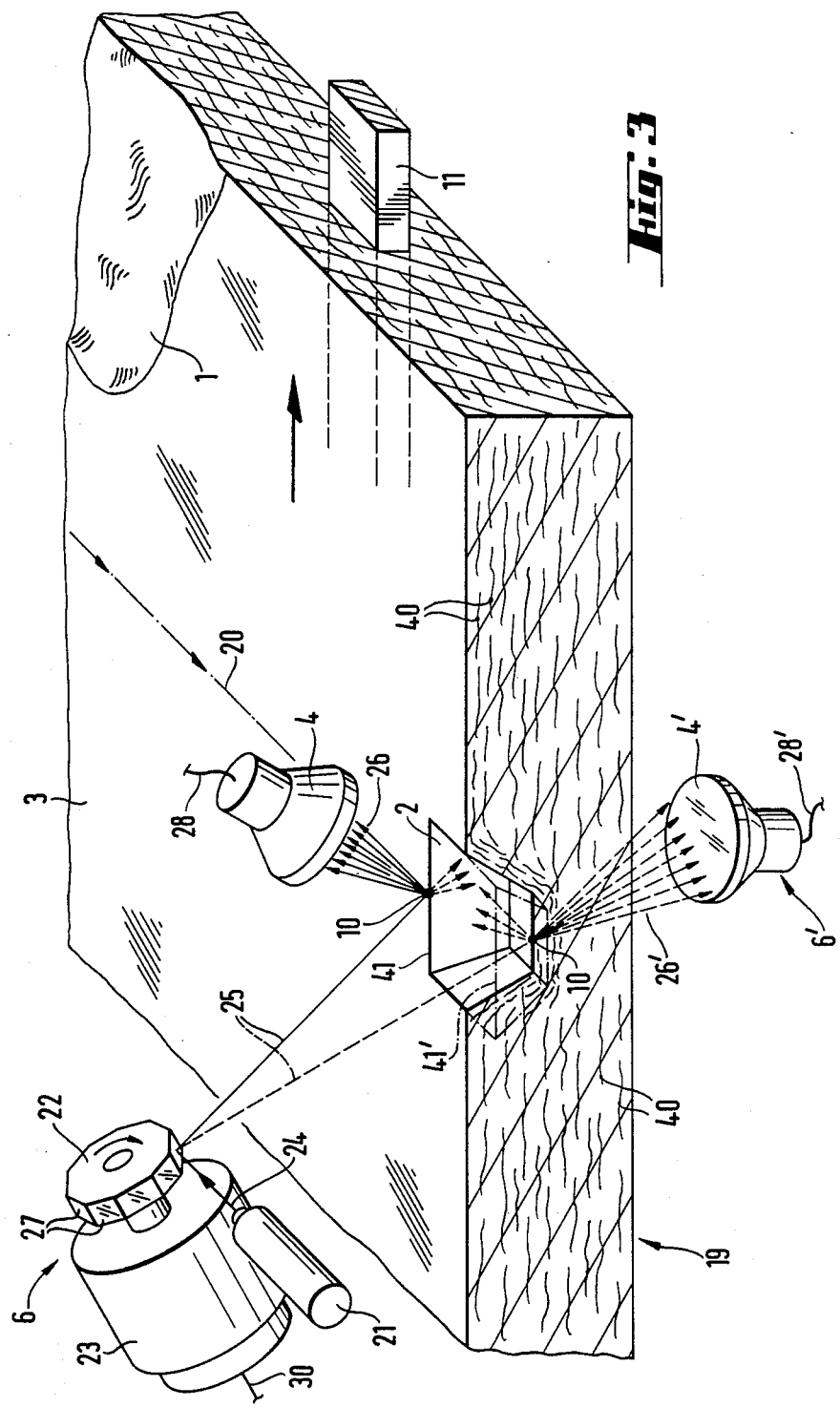
FIG. 3 is an enlarged perspective front view of a part of a security paper in cross section.
Figure 4:
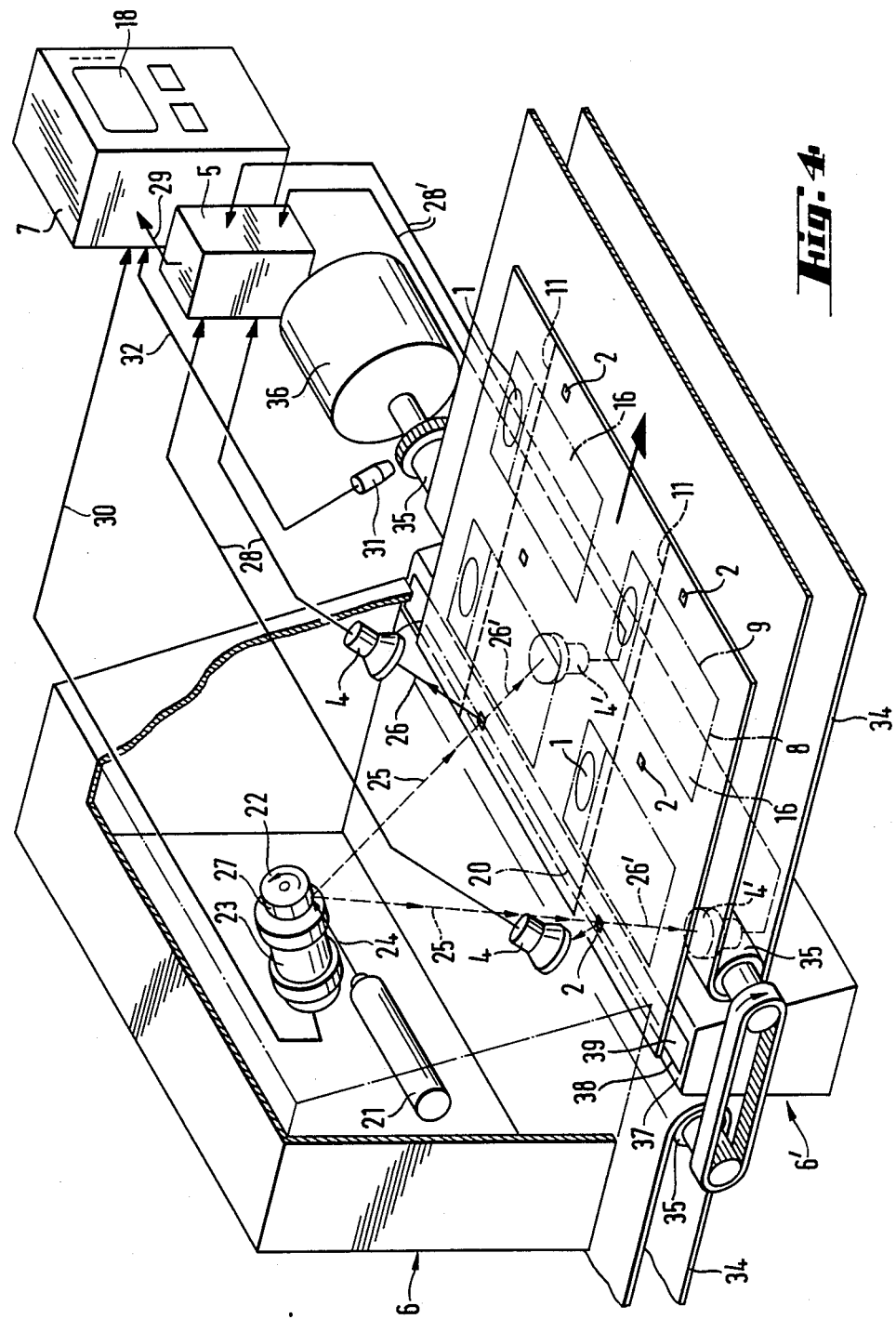
FIG. 4 is a schematic perspective view illustrating the test device of FIG. 1 with both the reflection and transmission measuring means.

FIG. 3 illustrates an enlarged cross section in perspective of a part of a security paper 19 wherein a measuring mark 2 is present. This measuring mark 2 consists of a pyramid truncated-like recess which has a square base face with a side length of 2 mm and which had been inserted during the forming of the paper web 3 in the wet portion of the machine. As can be clearly seen, this area of the paper web 3 has substantially fewer fibers 40, of which the paper web 3 is structured, than the remainder of the area. If a scanning beam 25 contacts a measuring mark 2, the light intensity of the reflecting light is changed as well as the light intensity of the transilluminated light. Since the measuring mark 2, deviating from the customary water marks, has been generated by a body limited by sharp edges and also has a relative large depth, a very strong edge impulse is generated at the moment when the scanning beam 25 passes the measuring marking edge 41, whereby in the microsecond range a second equally strong impulse occurs on a second measuring mark edge 41'. These impulses are then plottable when relative thick papers are used, which are tested in transmission or such having poor reflecting surfaces, since the edge impulse differs clearly, because it occurs impact like, from the possible uneven distribution of the fibers 40 within the paper web 3, the so-called cloudiness of the paper and also contrasts from the common water marks 1 which are disposed for marking security paper 19.

In order to prevent any overcuttings, the measuring marks 2 are disposed in the intermediary area 42 between the individual copies 16, i.e., in the area which after cutting of the printed sheet 33 becomes waste.

The terms and expression which have been employed are used as terms of description and not of limitation, and there is no intention in the use of such terms and expressions of excluding any equivalents of the features shown and described or portions thereof, it being recognized that various modifications are possible within the scope of the invention.

I claim:

1. A method of determining a dimension or a distortion error in a paper sheet comprising:
   (a) making a paper sheet including a security thread by a paper making process;
   (b) forming a water mark within a defined area of the paper sheet during the paper making process;
   (c) forming at least two sharp-edged recesses into the body of the paper sheet during the paper making process in an intermediate area outside said defined area, the depth of said recesses being 40 to 80% of the thickness of the paper sheet, said recesses being disposed in positions opposite to each other and each recess having a selected x and y position in the paper sheet;
   (d) scanning the paper sheet with a light means so that light strikes the recesses and is reflected as light pulses or permeates the paper sheet;
   (e) detecting the light pulses after the recesses are struck and evaluating the pulses in a computer means to establish a value of the pulses; and
   (f) comparing the value of the light pulses to values of the x and y positions of the recesses in said computer means, thereby determining any distortion in the paper sheet.

2. The method of claim 1, wherein each of said sharp-edged recesses comprises riser walls defining a recess having a substantially square-shaped base face, a side length of the face being in the range of from two to five millimeters.

3. The method according to claim 1 wherein the scanning step is performed with a flying light point means.

4. The method according to claim 3 wherein the flying light point means produces a light point having a diameter of from about 500 to 1,200 microns 5. The method of claim 1, wherein the scanning step further comprises scanning an edge of said recesses to produce an edge pulse, and evaluating said edge pulse in said computer means.

6. The method of claim 1, wherein the scanning step further comprises scanning an edge of said recess to form an edge pulse.

7. The method of claim 1, wherein said scanning step further comprises scanning another area of the paper sheet with a light sensitivity of the light means which is different in value from the light sensitivity of the light means which scans the intermediate area having two sharp-edged recess.

8. The method of claim 7, wherein the values of the light sensitivities are independently variable.

9. The method of claim 1, wherein said sharp-edged recesses are formed in areas which lie outside the security thread and outside water mark.

* * * * *